(12) United States Patent
Altmann et al.

(10) Patent No.: US 7,324,915 B2
(45) Date of Patent: Jan. 29, 2008

(54) DATA TRANSMISSION TO A POSITION SENSOR

(75) Inventors: Andres Claudio Altmann, Haifa (IL); Assaf Govari, Haifa (IL); Yaron Ephrath, Karkur (IL)

(73) Assignee: Biosense Webster, Inc., Diamond Bar, CA (US)

( * ) Notice: Subject to any disclaimer, the term of this patent is extended or adjusted under 35 U.S.C. 154(b) by 115 days.

(21) Appl. No.: 11/181,717

(22) Filed: Jul. 14, 2005

(65) Prior Publication Data

US 2007/0032960 A1    Feb. 8, 2007

(51) Int. Cl.
*G01C 9/00* (2006.01)

(52) U.S. Cl. .................. 702/150; 702/151; 702/152; 600/424

(58) Field of Classification Search ........... 702/150, 702/151, 152; 600/424; 324/207.15, 207.16, 324/207.17, 207.22, 207.23, 207.24, 207.25, 324/247
See application file for complete search history.

(56) References Cited

U.S. PATENT DOCUMENTS

| | | | | |
|---|---|---|---|---|
| 5,391,199 A * | 2/1995 | Ben-Haim | .................. | 607/122 |
| 5,443,489 A * | 8/1995 | Ben-Haim | .................. | 607/115 |
| 6,073,043 A * | 6/2000 | Schneider | .................. | 600/424 |
| 6,128,522 A * | 10/2000 | Acker et al. | ................ | 600/411 |
| 6,221,014 B1 * | 4/2001 | Bauer | ......................... | 600/439 |
| 6,239,724 B1 | 5/2001 | Doron et al. | | |
| 6,332,089 B1 | 12/2001 | Acker et al. | | |
| 6,409,674 B1 | 6/2002 | Brockway et al. | | |
| 6,470,207 B1 * | 10/2002 | Simon et al. | ............... | 600/426 |
| 6,618,612 B1 | 9/2003 | Acker et al. | | |
| 6,690,963 B2 | 2/2004 | Ben-Haim et al. | | |
| 6,774,624 B2 * | 8/2004 | Anderson et al. | ...... | 324/207.17 |
| 6,980,921 B2 * | 12/2005 | Anderson et al. | ........... | 702/150 |
| 7,096,148 B2 * | 8/2006 | Anderson et al. | ........... | 702/134 |
| 2002/0065455 A1 | 5/2002 | Ben-Haim et al. | | |
| 2003/0073901 A1 * | 4/2003 | Simon et al. | ............... | 600/424 |
| 2003/0120150 A1 | 6/2003 | Govari | | |
| 2004/0068178 A1 | 4/2004 | Govari | | |
| 2004/0106916 A1 * | 6/2004 | Quaid et al. | .................... | 606/1 |
| 2005/0033135 A1 * | 2/2005 | Govari et al. | .............. | 600/374 |
| 2005/0165297 A1 * | 7/2005 | Anderson et al. | .......... | 600/410 |
| 2005/0174235 A1 * | 8/2005 | Davis et al. | ........... | 340/539.13 |
| 2006/0074289 A1 * | 4/2006 | Adler et al. | ................ | 600/407 |
| 2006/0187026 A1 * | 8/2006 | Kochis | .................. | 340/539.13 |
| 2006/0241397 A1 * | 10/2006 | Govari et al. | .............. | 600/424 |
| 2006/0293593 A1 * | 12/2006 | Govari et al. | .............. | 600/424 |

OTHER PUBLICATIONS

U.S. Appl. No. 10/754,751, Biosense Webster, Inc., pending.
U.S. Appl. No. 11/062,258, Biosense Webster, Inc., pending.
U.S. Appl. No. 11/063,094, Biosense Webster, Inc., pending.

* cited by examiner

*Primary Examiner*—Carol S. W. Tsai
(74) *Attorney, Agent, or Firm*—Louis J. Capezzuto

(57) ABSTRACT

A method for transmitting control instructions to a sensor in a position tracking system includes generating a drive signal for driving a field generator. A control signal including the control instructions is superimposed on the drive signal. The field generator is driven with the drive signal, so as to generate a field to be sensed by the sensor. The field is detected at the sensor in order to determine position coordinates of the sensor and to demodulate the control signal so as to extract the control instructions. A functionality of the sensor is controlled based on the extracted control instructions.

18 Claims, 4 Drawing Sheets

DATA TRANSMISSION TO A POSITION SENSOR

FIELD OF THE INVENTION

The present invention relates generally to position tracking systems, and specifically to methods and devices for wireless communication with devices and tools that are used in position tracking systems.

BACKGROUND OF THE INVENTION

Various methods and systems are known in the art for tracking the coordinates of objects involved in medical procedures. For example, U.S. Pat. Nos. 5,391,199 and 5,443,489, whose disclosures are incorporated herein by reference, describe systems in which the coordinates of an intrabody probe are determined using one or more field transducers. Such systems are used for generating location information regarding a medical probe, such as a catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations. The sensor signals are processed in order to determine the coordinates of the probe in the external frame of reference.

Additional methods and systems that relate to magnetic position tracking are also described, for example, in PCT Patent Publication WO 96/05768, U.S. Pat. Nos. 6,690,963, 6,239,724, 6,618,612 and 6,332,089, and U.S. Patent Application Publications 2002/0065455 A1, 2003/0120150 A1 and 2004/0068178 A1, whose disclosures are all incorporated herein by reference. These publications describe methods and systems that track the position of intrabody objects such as cardiac catheters, orthopedic implants and medical tools used in different medical procedures.

In some medical applications, data is exchanged wirelessly between the external system and the intrabody object. For example, U.S. Pat. No. 6,409,674, whose disclosure is incorporated herein by reference, describes an implantable sensor device, such as a pressure monitor, which is implanted in the heart. The device wirelessly communicates blood pressure information or other physical parameters to a remote communication device. The wireless communication techniques noted in this patent include radio-telemetry, inductive coupling, passive transponders, and conductive communication using the body as a conductor. Another position tracking system that comprises wireless communication using inductive coupling is described in U.S. Patent Application Publication 2003/0120150 A1, whose disclosure is also incorporated herein by reference. The inventors describe a system in which a wireless transponder is fixed to an object. The transponder includes at least one sensor coil, in which a signal current flows responsively to sensed electromagnetic fields. A power coil receives an RF driving field and conveys electrical energy from the driving field to power the transponder. The power coil also transmits an output signal responsive to the signal current to a signal receiver, which processes the signal to determine coordinates of the object.

SUMMARY OF THE INVENTION

Embodiments of the present invention provide improved methods and devices for wireless communication in a position tracking system. In the embodiments disclosed herein-below, these methods are used for transmitting data, such as control data, to a sensor unit fitted into a tracked object in the position tracking system. Alternatively, these methods may be used, mutatis mutandis, to transmit data from a field generator on the tracked object to an external sensor. The disclosed methods and devices use the existing position sensor and processing circuits of the sensor control unit as the receiving circuit of a digital communication channel. Thus, the sensor unit is enabled to receive transmissions of control data with little or no addition of dedicated hardware for this purpose. Because the position-sensing circuitry of the sensor unit is used to extract both the position signals and the control signal, without the need for an additional antenna and receiver for receiving the control instructions, the sensor unit may be made smaller, lower in cost and more reliable.

In some embodiments, digital data is sent to the sensor unit from external field generators by modulating a control signal at an appropriate frequency that is not used for position sensing. The modulated control signal is combined with a drive signal that is normally used to drive the field generator. The position sensor and receiver circuits that are used for position sensing in the sensor unit receive the additional control signals as well. The sensor control unit digitizes, filters out and demodulates the control signal, to reproduce the transmitted digital data.

In some embodiments, different control instructions can be addressed to different sensor units by assigning a unique identification number (ID) to each sensor unit, or by using different modulation frequencies for different control signals.

In some embodiments, the sensor units are fitted into tracked objects such as orthopedic implants, implantable devices, intrabody catheters and endoscopes, as well as into various medical and surgical tools.

In another embodiment, a field generator is coupled to the tracked object and generates a magnetic field that is sensed by the external system. A method similar to that described above is used to transmit telemetry and control information from the tracked object without the need for additional transmitter hardware.

There is therefore provided, in accordance with an embodiment of the present invention, a method for transmitting control instructions to a sensor in a position tracking system, including:

generating a drive signal for driving a field generator;

superimposing a control signal including the control instructions on the drive signal;

driving the field generator with the drive signal, so as to generate a field to be sensed by the sensor;

at the sensor, detecting the field in order to determine position coordinates of the sensor and to demodulate the control signal so as to extract the control instructions; and controlling a functionality of the sensor based on the extracted control instructions.

In an embodiment, the drive signal has a drive frequency, and superimposing the control signal includes modulating the control instructions on a control sub-carrier having a control frequency, which is different from the drive frequency, so as to enable separation of the control signal from the drive signal.

In another embodiment, detecting the field includes producing a received signal responsive to the detected field, and extracting the control signal from the received signal.

Additionally or alternatively, extracting the control signal includes digitizing the received signal to produce a digitized signal, applying a Fast Fourier Transform (FFT) process to the digitized signal, and detecting energy in an FFT bin that corresponds to the control frequency.

In yet another embodiment, modulating the control instructions includes switching the control sub-carrier on and off responsively to a binary representation of the control instructions.

In still another embodiment, superimposing the control signal includes addressing a first control instruction to a first sensor and addressing a second control instruction, different from the first control instruction, to a second sensor.

In an embodiment, detecting the field includes detecting a first field component based on the control signal and a second field component associated with the position coordinates using a single coil in the sensor.

In another embodiment, controlling the functionality of the sensor includes at least one of controlling a timing of the sensor, calibrating the sensor and compensating for distortions in the detected field.

In yet another embodiment, the field includes a magnetic field.

There is also provided, in accordance with an embodiment of the present invention, a method for transmitting data from a tracked object in a position tracking system, including:

generating a drive signal for driving a field generator in the tracked object;

superimposing a data-carrying signal including the data on the drive signal;

driving the field generator with the drive signal, so as to generate a field to be sensed by one or more external receivers; and at the one or more external receivers, detecting the field in order to determine position coordinates of the tracked object and to demodulate the data-carrying signal so as to extract the data.

There is additionally provided, in accordance with an embodiment of the present invention, apparatus for transmitting control instructions to a sensor in a position tracking system, including:

a field generator, which is coupled to generate a field to be sensed by the sensor;

a signal generator unit, which is coupled to generate a drive signal for driving the field generator, while superimposing a control signal including the control instructions on the drive signal;

a sensor unit including a position sensor, which is coupled to detect the field, and a sensor control unit, which is coupled to generate position signals responsively to the detected field, to demodulate the control signal so as to extract the control instructions and to control a functionality of the sensor based on the extracted control instructions; and a processor, which is coupled to calculate position coordinates of the sensor responsively to the position signals.

There is further provided, in accordance with an embodiment of the present invention, apparatus for transmitting data from a tracked object in a position tracking system, including:

a field generator coupled to the tracked object, which is arranged to generate a field to be sensed by an external system;

a signal generator unit associated with the field generator, which is coupled to generate a drive signal for driving the field generator, while superimposing a data-carrying signal including the data on the drive signal; and one or more external receivers in the external system, which are coupled to detect the field in order to determine position coordinates of the tracked object and to demodulate the data-carrying signal so as to extract the data.

The present invention will be more fully understood from the following detailed description of the embodiments thereof, taken together with the drawings in which:

DETAILED DESCRIPTION OF EMBODIMENTS

In typical magnetic-based position sensing systems, such as the systems cited in the above-mentioned references, externally-generated magnetic fields induce position-responsive electrical currents in a receiver, such as a sensor coil, that is located within a sensor unit. In medical applications of such systems, the sensor unit is fitted inside a medical implant, a probe or another medical tool. A sensor control unit internal to the sensor unit acquires the signals from the receiver, computes position information, and transmits the information to the external system. The external system calculates the location and orientation of the sensor unit based on the position information received from the sensor unit. (Alternatively, as noted below, a field generator in the implant or tool may generate magnetic fields, which are sensed by a receiver outside the body.)

In certain applications, it is desirable to send data from the external system to the sensor unit. For example, the external system may transmit timing, calibration or other control commands to the sensor unit. In one embodiment, the external system may instruct the sensor unit to cancel a signal that is impaired by metal disturbances that distort the magnetic field. This signal cancellation improves the performance of the magnetic tracking system.

In some cases it is desired that the tracked sensor unit will have no wired connections to the external system. Consequently, data transmission to the sensor unit should be implemented wirelessly. A typical example is an orthopedic application, in which the sensor unit is fitted in an orthopedic implant that is implanted into a patient bone. Even in certain wired applications, such as catheters and endoscopes, it is sometimes beneficial to use wireless data transmission to the sensor unit. Using wireless transmission reduces the number of electrical wires that pass through the catheter or endoscope, thereby reducing its diameter. On the other hand, adding a separate wireless communication channel from the external system to the sensor unit is undesirable in terms of the added size and cost and the reduced reliability caused by the added antenna and other hardware components.

Figure 1:
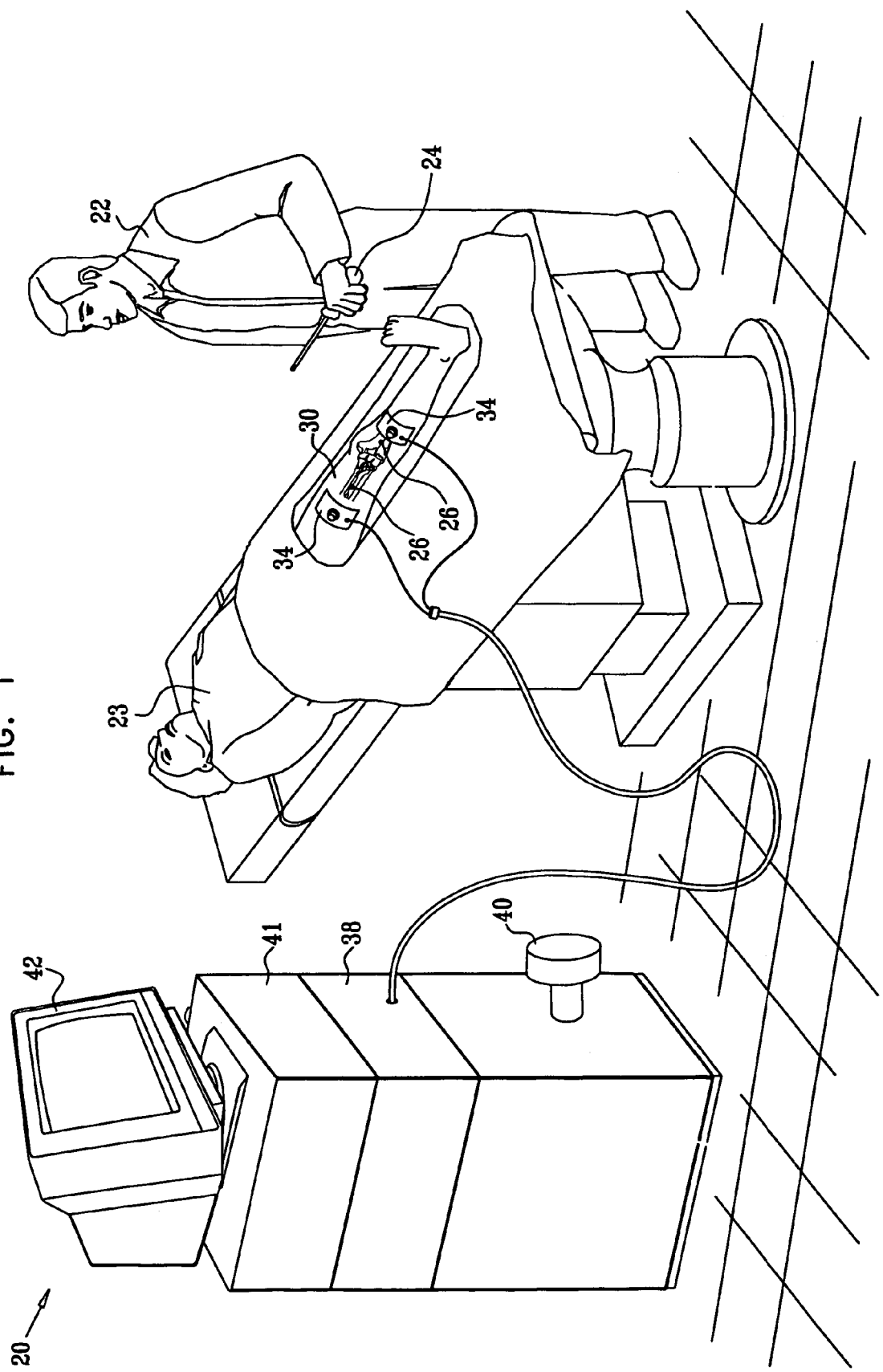
FIG. 1 is a schematic, pictorial illustration of a magnetic tracking system used in surgery, in accordance with an embodiment of the present invention.

FIG. 1 is a schematic, pictorial illustration of a magnetic tracking system 20 used in surgery, in accordance with an embodiment of the present invention. A surgeon 22 performs a medical procedure on a patient 23 using a medical tool 24. Implants 26 are introduced into the patient's body at a surgical site, which is located in this example in a leg 30 of the patient. The tracking system guides the surgeon in performing the procedure, in this example a knee-joint operation, by measuring and presenting the positions of implants 26 and tool 24. The system measures the location and orientation coordinates throughout a working volume that comprises the surgical site.

The coordinates of tool 24 and implants 26 are determined relative to field generators, such as location pads 34, which are fixed to the patient's body. In the example shown in FIG. 1, the pads are placed on the patient's calf and thigh, in proximity to implants 26. A signal generator unit 38 generates drive signals that drive the field generators, typically comprising field generating coils, in location pads 34. The location pads are typically connected by wires to unit 38, although a wireless connection is also feasible. The field generating coils generate magnetic fields throughout the working volume.

Implants 26 and tool 24 contain miniature, wireless sensor units, which are described in detail hereinbelow. Each sensor unit comprises a position sensor that is designed to sense the magnetic field in its vicinity. The magnetic fields generated by location pads 34 induce currents in the position sensors of the sensor units fitted into tool 24 and implants 26. In response to the induced currents, signal processing and transmitter circuits in each sensor unit generate and transmit position signals that are indicative of the location and orientation of the implant or tool.

The position signals are received by a wireless control unit 40, which is coupled to a computer 41. Computer 41 serves as the main system controller of system 20. The computer processes the received signals in order to calculate the relative location and orientation coordinates of tool 24 and implants 26. The results are typically presented to the surgeon on a display 42.

As part of the position tracking application, computer 41 generates control instructions, typically represented as digital data words, to be transmitted to the sensor units in implants 26 and/or tool 24. In one embodiment, the control instructions comprise timing instructions. Additionally or alternatively, the control instructions comprise calibration information for the sensor units. In other embodiments, the control instructions enable the sensor unit to mitigate the effects of distortion in the applied magnetic fields. Such distortions are typically caused by the introduction of metallic objects into the working volume. In these embodiments, the computer instructs the sensor unit to cancel or compensate for a signal that is impaired by metal disturbance. Any other type of control instructions can be transmitted to the sensor unit using the disclosed methods. Control instructions may, for example, instruct the sensor to start or stop its transmission, to wake-up, to switch to a low power mode or otherwise change its mode of operation, or to change its operating frequency.

In order to transmit the instructions to the sensor unit, signal generator unit 38 generates a modulated control signal, as will be explained in detail below. The control signal is modulated on one or more of the drive signals that are used to drive the field generating coils in location pads 34. In other words, the control signal modulates one or more of the magnetic fields transmitted to the sensor unit. In one embodiment, as described above and shown in FIG. 3 below, the modulation of the drive signals and the superposition of the control signal on the drive signal are carried out in signal generator unit 38. The modulated drive signals are sent to location pads 34 via the interconnecting wires. In an alternative embodiment, the location pads receive the control instructions. The modulation and superposition functions are then carried out by the location pads.

When the sensor unit senses the magnetic fields, it demodulates the control signal and decodes the control instructions.

In one embodiment, the location pads generate electromagnetic fields having different frequencies. Typical frequencies are chosen in the range 100 Hz-30 kHz (often referred to as the audio range), although other frequency ranges can also be used. The control signal is typically modulated on a sub-carrier having a different audio frequency that is not used by the drive signals. The frequency of the control sub-carrier is chosen to allow sufficient frequency separation from the frequencies used for position sensing. Sufficient separation enables the receiver circuitry in the sensor unit to filter out and extract the control signal, as will be explained below. Typically, the frequencies used by the system for position sensing and for transmitting the control signal are set by computer 41.

In some embodiments, signal generator unit 38 sends different control signals to different sensor units. In one embodiment, control signals addressed to different sensor units use different sub-carrier frequencies. Additionally or alternatively, each sensor unit is assigned a unique ID, and the control signal uses a suitable protocol for addressing the desired sensor unit. Alternatively, any other suitable addressing method can be used.

The system shown in FIG. 1 is related to an orthopedic application. Further details regarding position tracking systems of this sort can be found in U.S. patent application Ser. No. 11/063,094. Another, similar system for orthopedic applications, in which the principles of the present invention may be implemented, is described in U.S. Provisional Patent Application No. 60/550,924, filed Mar. 5, 2004, now filed as U.S. patent application Ser. No. 11/062,258. All of these applications are assigned to the assignee of the present patent application, and their disclosures are incorporated herein by reference.

The exemplary system shown in FIG. 1, however, was chosen purely for the sake of conceptual clarity. Other system configurations will be apparent to those skilled in the art and are considered to be within the scope of the present invention. For example, any number of implants 26, medical tools 24 and location pads 34 can be used. Sensor units can be fitted into other types of implants and medical tools, as well as into invasive medical instruments such as catheters and endoscopes. The location pads may be attached to the patient's body using any suitable technique, as is known in the art. Alternatively, the location pads can be mounted on a suitable external structure.

Location pads 34 and the sensor units in implants 26 and tool 24 can be designed to either transmit or receive magnetic fields. In other words, if the sensor units in implants 26 and in tool 24 are configured to receive magnetic fields, then location pads 34 are configured to generate fields. Alternatively, the location pads may be configured to sense fields generated by field generators fitted into the implants and the tool. In the description that follows it is assumed that location pads 34 generate the magnetic fields, which are received by the sensor units in implants 26 and in tool 24. In configurations in which the roles of transmitter and receiver are reversed, the principles of the present invention can be used to transmit control and/or telemetry information from the tracked objects to the external system.

Figure 2:
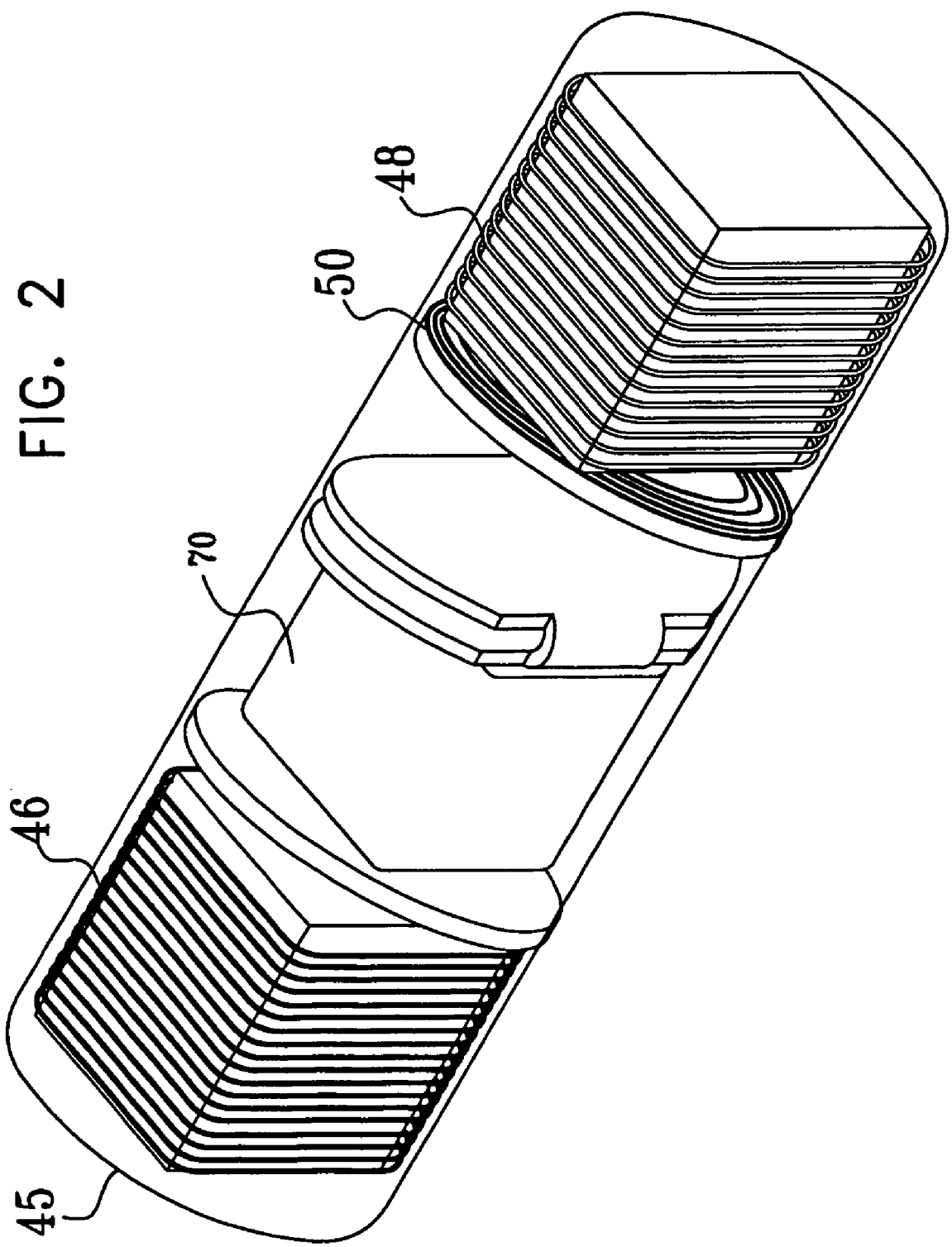
FIG. 2 is a schematic, pictorial illustration showing details of a sensor unit, in accordance with an embodiment of the present invention.

FIG. 2 is a schematic, pictorial illustration of a sensor unit 45 that is contained in implant 26, in accordance with an embodiment of the present invention. Sensor unit 45 comprises a position sensor 46, typically comprising three position coils that sense the applied magnetic fields in the vicinity of the sensor. Power coils 48 serve as a power source for sensor unit 45. The power coils typically receive radio frequency (RF) energy by inductive coupling from an external driving antenna (which may be a part of wireless control unit 40 shown in FIG. 1). Optionally, the sensor and power coils may be wound on a common core, as described in U.S. patent application Ser. No. 10/754,751. Alternatively, power may be supplied by a battery (not shown) in sensor unit 45 or by other suitable means. A communication coil 50 is used to transmit the position signals from the sensor unit to wireless control unit 40. Alternatively, either the coils of sensor 46 or power coils 48 may also be used for transmitting the position signals, obviating the need for the separate communication coil.

Position sensor 46 and coils 48 and 50 are coupled to a sensor control unit 70. The magnetic fields generated by location pads 34 induce time-varying signal voltages across the position coils in position sensor 46, as described above. Unit 70 receives the signal voltages and generates position signals in response to these voltages. Unit 70 drives communication coil 50 to transmit the position signals to a receiving antenna in the external system, typically in wireless control unit 40.

FIG. 2 shows an exemplary sensor unit configuration. As noted above, other electrical and mechanical configurations can be used to implement sensor unit 45 to suit different medical implants and instruments. Some exemplary sensor unit configurations are given in the above-mentioned patent application Ser. No. 11/062,258.

Figure 3:
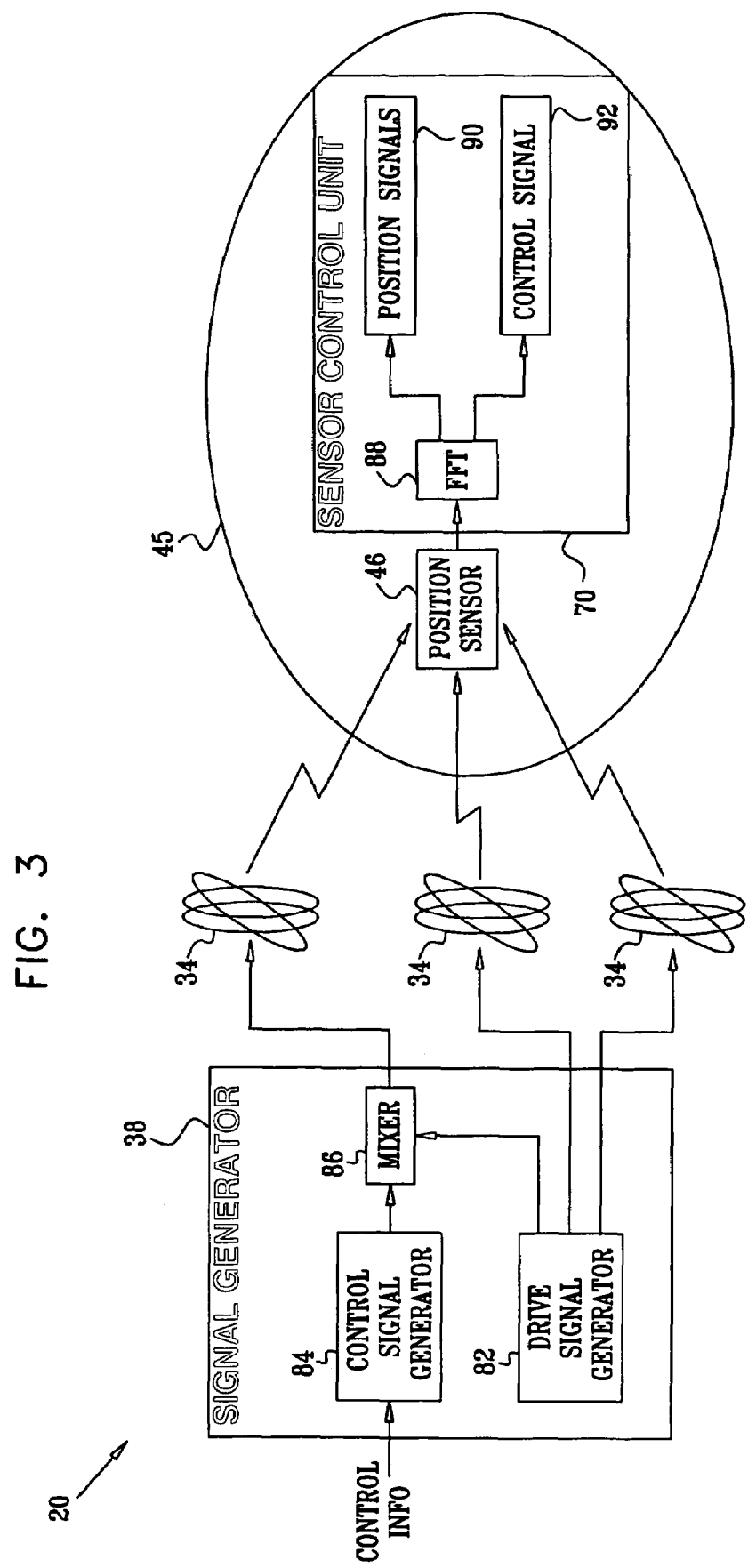
FIG. 3 is a block diagram that schematically illustrates a magnetic tracking system, in accordance with an embodiment of the present invention.

FIG. 3 is a block diagram that schematically shows functional elements of magnetic tracking system 20, in accordance with an embodiment of the present invention. A drive signal generator 82 in signal generator unit 38 generates drive signals so as to drive the field generating coils in location pads 34, as described above. A control signal generator 84 in signal generator unit 38 accepts control instructions from computer 41 and generates a control signal, typically modulated on a sub-carrier having a suitable audio frequency. In one exemplary configuration the drive signals use frequencies in the range of 1-3 KHz while the control signal uses a frequency of 8 KHz. A mixer 86 combines the control signal with at least one of the drive signals. The drive signals are then used to drive the field generating coils in location pads 34. (FIG. 3 shows three location pads 34, but any number of pads can be used, as explained in the description of FIG. 1 above.)

In one embodiment, the control signal generator generates the control signal by switching the sub-carrier signal on and off at a predetermined bit-rate, according to a binary coded representation of the control instructions. This modulation is often referred to as on-off keying (OOK).

In a disclosed embodiment, the signal generator unit combines the control signal with two or more drive signals. The control signal combined with each drive signal may use a different sub-carrier frequency. Additionally or alternatively, different control instructions can be transmitted on different drive signals. Such configuration can be used, for example, to facilitate sending different instructions to different sensor units.

The magnetic fields generated by pads 34 are sensed by position sensor 46 of sensor unit 45 and the corresponding voltages sent to sensor control unit 70 for processing. The sensor control unit amplifies, filters and digitizes the received signal to produce a digitized signal. (The analog circuits and analog/digital converter used for this purpose are omitted from FIG. 3 for the sake of simplicity.) A digital filter 88 in the sensor control unit filters out the control signal from the digitized signal, typically using a Fast Fourier Transform (FFT) process. The FFT process can be implemented either in dedicated hardware or as a software process. Alternatively, any other suitable filtering process can be used to implement filter 88. In an alternative embodiment, filter 88 comprises an analog filter, and digitization of the received control signal is performed after filtering.

The sensor control unit then demodulates the filtered signals and produces separate position signals 90 and a control signal 92. Position signals 90 are typically transmitted to wireless control unit 40. The sensor control unit demodulates the control signal to reproduce the control instructions. In the embodiment that uses on-off keying for modulating the control signal, demodulating the control signal typically comprises detecting the presence or absence of signal energy in an FFT bin corresponding to the sub-carrier frequency.

The control instructions are then used to control, calibrate or otherwise operate the sensor unit. Using the disclosed configuration, the position-sensing circuitry of the sensor unit is used to extract both position signals 90 and control signal 92, without the need for an additional antenna and receiver for receiving the control instructions. This configuration enables the design of smaller, lower cost and more reliable sensor units.

Figure 4:
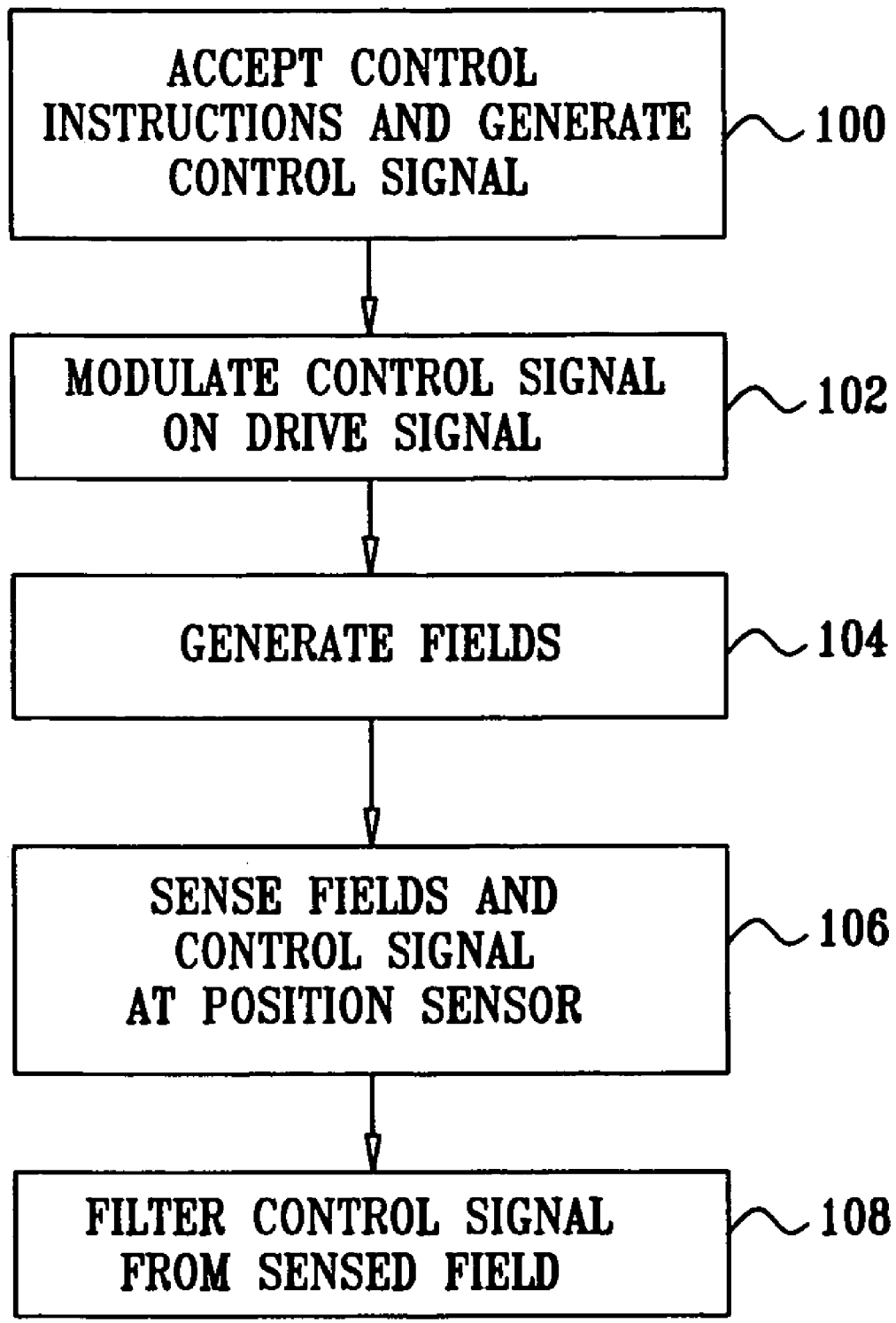
FIG. 4 is a flow chart that schematically illustrates a method for communicating with a sensor unit, in accordance with an embodiment of the present invention.

FIG. 4 is a flow chart that schematically illustrates a method for communicating with sensor unit 45, in accordance with an embodiment of the present invention. The method begins with signal generator unit 38 accepting control instructions, at a control generation step 100. Control signal generator 84 generates a control signal, typically by modulating a sub-carrier having a suitable audio frequency, as described above.

Signal generator unit 38 combines the control signal with one or more of the drive signals generated by drive signal generator 82 using mixer 86, at a combining step 102. The signal generator unit sends the drive signals to location pads 34. Location pads 34 generate magnetic fields responsively to the drive signals, at a field generation step 104. Position sensor 46 in sensor unit 45 senses the magnetic field in its vicinity, at a sensing step 106. The position sensor generates time-varying voltages responsively to the sensed field. The voltages comprise components that correspond to the different drive signals and to the transmitted control signal. Sensor control unit 70 receives the voltages and extracts the position signals and the control signal, at an extraction step 108. As explained above, the control unit amplifies and digitizes the induced voltages. The digitized signal is then filtered, typically using FFT, to produce the position signals and control signal. The position signals are transmitted, via communication coil 50 and wireless control unit 40, to computer 41 for processing. Finally, the control unit demodulates the control signal to reproduce the control instructions transmitted to the sensor unit.

Although the disclosed methods and systems mainly address data transmission to an intrabody sensor in a magnetic tracking system, the principles of the present invention can be used in other applications. For example, control signals may be modulated onto fields generated for purposes of position sensing in other types of tracking systems, such as ultrasonic and optical tracking systems. Other applications may also include radio frequency identification (RFID) or other tagging systems, such as magnetically-coupled tagging systems.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for transmitting control instructions to a sensor in a position tracking system, comprising:
generating a drive signal for driving a field generator;
superimposing a control signal comprising the control instructions on the drive signal;
driving the field generator with the drive signal, so as to generate a field to be sensed by the sensor;
at the sensor, detecting the field in order to determine position coordinates of the sensor and to demodulate the control signal so as to extract the control instructions; and
controlling a functionality of the sensor based on the extracted control instructions; and wherein the drive signal has a drive frequency, and wherein superimposing the control signal comprises modulating the control instructions on a control sub-carrier having a control frequency, which is different from the drive frequency, so as to enable separation of the control signal from the drive signal.

2. The method according to claim 1, wherein detecting the field comprises producing a received signal responsive to the detected field, and extracting the control signal from the received signal.

3. The method according to claim 2, wherein extracting the control signal comprises digitizing the received signal to produce a digitized signal, applying a Fast Fourier Transform (FFT) process to the digitized signal, and detecting energy in an FFT bin that corresponds to the control frequency.

4. The method according to claim 1, wherein modulating the control instructions comprises switching the control sub-carrier on and off responsively to a binary representation of the control instructions.

5. The method according to claim 1, wherein superimposing the control signal comprises addressing a first control instruction to a first sensor and addressing a second control instruction, different from the first control instruction, to a second sensor.

6. The method according to claim 1, wherein detecting the field comprises detecting a first field component based on the control signal and a second field component associated with the position coordinates using a single coil in the sensor.

7. The method according to claim 1, wherein controlling the functionality of the sensor comprises at least one of controlling a timing of the sensor, calibrating the sensor and compensating for distortions in the detected field.

8. The method according to claim 1, wherein the field comprises a magnetic field.

9. A method for transmitting data from a tracked object in a position tracking system, comprising:
generating a drive signal for driving a field generator in the tracked object;
superimposing a data-carrying signal comprising the data on the drive signal;
driving the field generator with the drive signal, so as to generate a field to be sensed by one or more external receivers; and
at the one or more external receivers, detecting the field in order to determine position coordinates of the tracked object and to demodulate the data-carrying signal so as to extract the data; and
wherein the drive signal has a drive frequency, and
wherein superimposing the data-carrying signal comprises modulating the data on a control sub-carrier having a control frequency, which is different from the drive frequency, so as to enable separation of the data-carrying signal from the drive signal.

10. Apparatus for transmitting control instructions to a sensor in a position tracking system, comprising:
a field generator, which is coupled to generate a field to be sensed by the sensor;
a signal generator unit, which is coupled to generate a drive signal for driving the field generator, while superimposing a control signal comprising the control instructions on the drive signal;
a sensor unit comprising a position sensor, which is coupled to detect the field, and a sensor control unit, which is coupled to generate position signals responsively to the detected field, to demodulate the control signal so as to extract the control instructions and to control a functionality of the sensor based on the extracted control instructions; and
a processor, which is coupled to calculate position coordinates of the sensor responsively to the position signals; and
wherein the signal generator unit is coupled to generate the drive signal at a drive frequency and to modulate the control instructions on a control sub-carrier having a control frequency, which is different from the drive frequency, so as to enable separation of the control signal from the drive signal.

11. The apparatus according to claim 10, wherein the position sensor is coupled to produce a received signal responsive to the detected field, and wherein the sensor control unit is coupled to extract the control signal from the received signal.

12. The apparatus according to claim 11, wherein the sensor control unit is coupled to digitize the received signal so as to produce a digitized signal, to apply a Fast Fourier Transform (FFT) process to the digitized signal, and to detect energy in an FFT bin that corresponds to the control frequency, so as to extract the control signal.

13. The apparatus according to claim 10, wherein the signal generator unit is coupled to switch the control sub-carrier on and off responsively to a binary representation of the control instructions, so as to modulate the control signal.

14. The apparatus according to claim 10, wherein the processor is coupled to address a first control instruction to a first sensor and to address a second control instruction, different from the first control instruction, to a second sensor.

15. The apparatus according to claim 10, wherein the position sensor comprises a coil, which is coupled to receive both a first field component based on the control signal and a second field component associated with the position coordinates.

16. The apparatus according to claim 10, wherein the sensor control unit is coupled to perform, responsively to the control instructions, at least one of controlling a timing of the sensor unit, calibrating the sensor unit and compensating for distortions in the detected field.

17. The apparatus according to claim 10, wherein the field comprises a magnetic field.

18. Apparatus for transmitting data from a tracked object in a position tracking system, comprising:
- a field generator coupled to the tracked object, which is arranged to generate a field to be sensed by an external system;
- a signal generator unit associated with the field generator, which is coupled to generate a drive signal for driving the field generator, while superimposing a data-carrying signal comprising the data on the drive signal; and
- one or more external receivers in the external system, which are coupled to detect the field in order to determine position coordinates of the tracked object and to demodulate the data-carrying signal so as to extract the data; and wherein the drive signal has a drive frequency, and wherein superimposing the data-carrying signal comprises modulating the data on a control sub-carrier having a control frequency, which is different from the drive frequency, so as to enable separation of the data-carrying signal from the drive signal.

* * * * *